US012678620B2

(12) United States Patent
Wasserman et al.

(10) Patent No.: US 12,678,620 B2
(45) Date of Patent: Jul. 14, 2026

(54) REDUCING ELECTROSENSATION WHILE TREATING A SUBJECT USING ALTERNATING ELECTRIC FIELDS BY CONTROLLING RAMP-UP CHARACTERISTICS

(71) Applicant: Novocure GmbH, Root D4 (CH)

(72) Inventors: Yoram Wasserman, Haifa (IL); Michael Shtotland, Haifa (IL)

(73) Assignee: Novocure GmbH, Baar (CH)

( * ) Notice: Subject to any disclaimer, the term of this patent is extended or adjusted under 35 U.S.C. 154(b) by 354 days.

(21) Appl. No.: 18/374,081

(22) Filed: Sep. 28, 2023

(65) Prior Publication Data

US 2024/0108888 A1 Apr. 4, 2024

Related U.S. Application Data

(60) Provisional application No. 63/411,725, filed on Sep. 30, 2022.

(51) Int. Cl.
| | |
|---|---|
| *A61N 1/00* | (2006.01) |
| *A61N 1/32* | (2006.01) |
| *A61N 1/36* | (2006.01) |

(52) U.S. Cl.
CPC ......... *A61N 1/323* (2013.01); *A61N 1/36002* (2017.08)

(58) Field of Classification Search
None
See application file for complete search history.

(56) References Cited

U.S. PATENT DOCUMENTS

| | | | |
|---|---|---|---|
| 6,868,289 | B2 | 3/2005 | Palti |
| 7,016,725 | B2 | 3/2006 | Palti |
| 7,089,054 | B2 | 8/2006 | Palti |
| 7,136,699 | B2 | 11/2006 | Palti |
| 7,333,852 | B2 | 2/2008 | Palti |
| 7,467,011 | B2 | 12/2008 | Palti |
| 7,519,420 | B2 | 4/2009 | Palti |
| 7,565,205 | B2 | 7/2009 | Palti |
| 7,565,206 | B2 | 7/2009 | Palti |
| 7,599,745 | B2 | 10/2009 | Palti |
| 7,599,746 | B2 | 10/2009 | Palti |
| 7,706,890 | B2 | 4/2010 | Palti |
| 7,715,921 | B2 | 5/2010 | Palti |
| 7,805,201 | B2 | 9/2010 | Palti |
| 7,890,183 | B2 | 2/2011 | Palti et al. |

(Continued)

FOREIGN PATENT DOCUMENTS

WO WO-2023116670 A1 * 6/2023 ........... A61N 1/3603

OTHER PUBLICATIONS

International Search Report and Written Opinion issued in application No. PCT/IB2023/059656 dated Jan. 3, 2024.

*Primary Examiner* — William J Levicky
*Assistant Examiner* — Ananta A Gupta
(74) *Attorney, Agent, or Firm* — Potomac Law Group, PLLC

(57) ABSTRACT

When transducer arrays (i.e., arrays of electrode elements) are used to apply alternating electric fields to a subject's body, the subject may experience electrosensation. This electrosensation can be ameliorated by changing the way the voltage ramps up from zero to its peak when the AC voltage is first applied to any given transducer array, and also when the alternating electric field switches direction.

14 Claims, 4 Drawing Sheets

(56) References Cited

U.S. PATENT DOCUMENTS

| | | | |
|---|---|---|---|
| 7,912,540 | B2 | 3/2011 | Palti |
| 7,917,227 | B2 | 3/2011 | Palti |
| 8,019,414 | B2 | 9/2011 | Palti |
| 8,027,738 | B2 | 9/2011 | Palti |
| 8,170,684 | B2 | 5/2012 | Palti |
| 8,175,698 | B2 | 5/2012 | Palti et al. |
| 8,229,555 | B2 | 7/2012 | Palti |
| RE43,618 | E | 8/2012 | Palti |
| 8,244,345 | B2 | 8/2012 | Palti |
| 8,406,870 | B2 | 3/2013 | Palti |
| 8,447,395 | B2 | 5/2013 | Palti et al. |
| 8,447,396 | B2 | 5/2013 | Palti et al. |
| 8,465,533 | B2 | 6/2013 | Palti |
| 8,706,261 | B2 | 4/2014 | Palti |
| 8,715,203 | B2 | 5/2014 | Palti |
| 8,718,756 | B2 | 5/2014 | Palti |
| 8,764,675 | B2 | 7/2014 | Palti |
| 9,023,090 | B2 | 5/2015 | Palti |
| 9,023,091 | B2 | 5/2015 | Palti |
| 9,039,674 | B2 | 5/2015 | Palti et al. |
| 9,056,203 | B2 | 6/2015 | Palti et al. |
| 9,440,068 | B2 | 9/2016 | Palti et al. |
| 9,655,669 | B2 | 5/2017 | Palti et al. |
| 9,750,934 | B2 | 9/2017 | Palti et al. |
| 9,910,453 | B2 | 3/2018 | Wasserman et al. |
| 10,188,851 | B2 | 1/2019 | Wenger et al. |
| 10,441,776 | B2 | 10/2019 | Kirson et al. |
| 10,779,875 | B2 | 9/2020 | Palti et al. |
| 10,967,167 | B2 | 4/2021 | Hagemann et al. |
| 11,103,698 | B2 | 8/2021 | Chang et al. |
| 11,191,956 | B2 | 12/2021 | Giladi et al. |
| 11,395,916 | B2 | 7/2022 | Wasserman et al. |
| 2004/0176804 | A1 | 9/2004 | Palti |
| 2005/0209642 | A1 | 9/2005 | Palti |
| 2006/0167499 | A1 | 7/2006 | Palti |
| 2006/0276858 | A1 | 12/2006 | Palti |
| 2007/0225766 | A1 | 9/2007 | Palti |
| 2007/0239213 | A1 | 10/2007 | Palti |
| 2008/0004675 | A1 | 1/2008 | King et al. |
| 2009/0076366 | A1 | 3/2009 | Palti |
| 2012/0029419 | A1 | 2/2012 | Palti |
| 2012/0283726 | A1 | 11/2012 | Palti |
| 2014/0330268 | A1 | 11/2014 | Palti et al. |
| 2017/0120041 | A1 | 5/2017 | Wenger et al. |
| 2017/0215939 | A1 | 8/2017 | Palti et al. |
| 2017/0281934 | A1 | 10/2017 | Giladi et al. |
| 2018/0001075 | A1 | 1/2018 | Kirson et al. |
| 2018/0008708 | A1 | 1/2018 | Giladi et al. |
| 2018/0050200 | A1 | 2/2018 | Wasserman et al. |
| 2018/0160933 | A1 | 6/2018 | Urman et al. |
| 2018/0202991 | A1 | 7/2018 | Giladi et al. |
| 2018/0280687 | A1 | 10/2018 | Carter et al. |
| 2019/0117956 | A1 | 4/2019 | Wenger et al. |
| 2019/0117963 | A1 | 4/2019 | Travers et al. |
| 2019/0117970 | A1 | 4/2019 | Schmidt et al. |
| 2019/0224474 | A1 | 7/2019 | Yang et al. |
| 2019/0308016 | A1 | 10/2019 | Wenger et al. |
| 2020/0001069 | A1 | 1/2020 | Kirson et al. |
| 2020/0009376 | A1 | 1/2020 | Chang et al. |
| 2020/0009377 | A1 | 1/2020 | Chang et al. |
| 2020/0016067 | A1 | 1/2020 | Gotlib et al. |
| 2020/0023179 | A1 | 1/2020 | Bomzon et al. |
| 2020/0061360 | A1 | 2/2020 | Hagemann et al. |
| 2020/0061361 | A1 | 2/2020 | Hagemann et al. |
| 2020/0069937 | A1 | 3/2020 | Naveh et al. |
| 2020/0078582 | A1 | 3/2020 | Alon et al. |
| 2020/0108031 | A1 | 4/2020 | Borst et al. |
| 2020/0114141 | A1 | 4/2020 | Bomzon et al. |
| 2020/0114142 | A1 | 4/2020 | Bomzon et al. |
| 2020/0121728 | A1 | 4/2020 | Wardak et al. |
| 2020/0129761 | A1 | 4/2020 | Bomzon et al. |
| 2020/0146586 | A1 | 5/2020 | Naveh et al. |
| 2020/0155835 | A1 | 5/2020 | Wasserman et al. |
| 2020/0171297 | A1 | 6/2020 | Kirson et al. |
| 2020/0179512 | A1 | 6/2020 | Giladi et al. |
| 2020/0219261 | A1 | 7/2020 | Shamir et al. |
| 2020/0269037 | A1 | 8/2020 | Hagemann et al. |
| 2020/0269041 | A1 | 8/2020 | Zeevi et al. |
| 2020/0269042 | A1 | 8/2020 | Giladi et al. |
| 2020/0368525 | A1 | 11/2020 | Maag et al. |
| 2021/0031031 | A1 | 2/2021 | Wasserman et al. |
| 2021/0038584 | A1 | 2/2021 | Voloshin-Sela |
| 2021/0038892 | A1 | 2/2021 | Valcke |
| 2021/0060334 | A1 | 3/2021 | Avraham et al. |
| 2021/0069503 | A1 | 3/2021 | Tran et al. |
| 2021/0138233 | A1 | 5/2021 | Deslauriers |
| 2021/0162228 | A1 | 6/2021 | Urman et al. |
| 2021/0177492 | A1 | 6/2021 | Travers et al. |
| 2021/0187277 | A1 | 6/2021 | Wasserman et al. |
| 2021/0196348 | A1 | 7/2021 | Wasserman |
| 2021/0199640 | A1 | 7/2021 | Patel et al. |
| 2021/0203250 | A1 | 7/2021 | Wasserman |
| 2021/0268247 | A1 | 9/2021 | Story et al. |
| 2021/0299439 | A1 | 9/2021 | Shamir et al. |
| 2021/0299440 | A1 | 9/2021 | Deslauriers et al. |
| 2021/0308446 | A1 | 10/2021 | Alon et al. |
| 2021/0330950 | A1 | 10/2021 | Hagemann et al. |
| 2021/0346694 | A1 | 11/2021 | Wasserman et al. |
| 2021/0379362 | A1 | 12/2021 | Smith et al. |
| 2021/0408383 | A1 | 12/2021 | Kalra et al. |
| 2022/0088403 | A1 | 3/2022 | Voloshin-Sela et al. |
| 2022/0095997 | A1 | 3/2022 | Wasserman |
| 2022/0096821 | A1 | 3/2022 | Kirson et al. |
| 2022/0096829 | A1 | 3/2022 | Farber et al. |
| 2022/0118249 | A1 | 4/2022 | Bomzon et al. |
| 2022/0161028 | A1* | 5/2022 | Giladi ............... A61N 1/36002 |
| 2022/0193435 | A1 | 6/2022 | Wasserman et al. |
| 2022/0203111 | A1 | 6/2022 | Carlson |
| 2022/0267445 | A1 | 8/2022 | Tran et al. |
| 2022/0280787 | A1 | 9/2022 | Bomzon et al. |
| 2022/0288395 | A1 | 9/2022 | Voloshin-Sela et al. |
| 2022/0313992 | A1 | 10/2022 | Wasserman |
| 2022/0323753 | A1 | 10/2022 | Voloshin-Sela et al. |
| 2022/0387784 | A1 | 12/2022 | Kirson et al. |
| 2022/0395699 | A1 | 12/2022 | Doyle |
| 2022/0409893 | A1 | 12/2022 | Wasserman et al. |
| 2023/0000384 | A1 | 1/2023 | Wasserman et al. |
| 2023/0001197 | A1 | 1/2023 | Wasserman et al. |
| 2023/0001221 | A1 | 1/2023 | Farber |
| 2023/0009366 | A1 | 1/2023 | Voloshin-Sela et al. |
| 2023/0019638 | A1 | 1/2023 | Wasserman |
| 2023/0037806 | A1 | 2/2023 | Wasserman et al. |
| 2023/0043071 | A1 | 2/2023 | Wasserman et al. |
| 2023/0098801 | A1 | 3/2023 | Carlson |
| 2023/0141087 | A1 | 5/2023 | Giladi et al. |
| 2023/0149708 | A1 | 5/2023 | O'connell et al. |
| 2023/0168242 | A1 | 6/2023 | Sarkisian et al. |
| 2023/0188055 | A1 | 6/2023 | Wasserman |
| 2023/0191123 | A1 | 6/2023 | Wasserman et al. |
| 2023/0201616 | A1 | 6/2023 | Carlson |
| 2023/0218912 | A1 | 7/2023 | Giladi et al. |
| 2023/0241374 | A1 | 8/2023 | Shnaiderman et al. |
| 2023/0248826 | A1 | 8/2023 | Giladi et al. |
| 2023/0248969 | A1 | 8/2023 | Wasserman et al. |
| 2023/0310848 | A1 | 10/2023 | Voloshin-Sela et al. |
| 2023/0310849 | A1 | 10/2023 | Wasserman et al. |
| 2023/0310877 | A1 | 10/2023 | Giladi |

* cited by examiner

REDUCING ELECTROSENSATION WHILE TREATING A SUBJECT USING ALTERNATING ELECTRIC FIELDS BY CONTROLLING RAMP-UP CHARACTERISTICS

CROSS REFERENCE TO RELATED APPLICATIONS

This application claims the benefit of U.S. Provisional Application 63/411,725, filed Sep. 30, 2022, is incorporated herein by reference in its entirety.

BACKGROUND

Tumor Treating Fields (TTFields) therapy is a proven approach for treating tumors using alternating electric fields at frequencies between 50 kHz and 1 MHz (e.g., 150-200 kHz). In the prior art Optune® system, TTFields are delivered to patients via four transducer arrays that are placed on the patient's skin near the tumor. The transducer arrays are arranged in two pairs, with one pair of transducer arrays positioned to the left and right of the tumor, and the other pair of transducer arrays positioned anterior and posterior to the tumor. Each transducer array is connected via a multi-wire cable to an AC signal generator. The AC signal generator (a) sends an AC current through the anterior/posterior (A/P) pair of transducer arrays for 1 second, which induces an electric field with a first direction through the tumor; then (b) sends an AC current through the left/right (L/R) pair of arrays for 1 second, which induces an electric field with a second direction through the tumor; then repeats steps (a) and (b) for the duration of the treatment. Each transducer array includes a plurality (e.g., between 9 and 30) of electrode elements.

Alternating electric fields can also be used to treat medical conditions other than tumors. For example, as described in U.S. Pat. No. 10,967,167 (which is incorporated herein by reference in its entirety), alternating electric fields can be used to increase the permeability of the blood brain barrier (BBB) so that, e.g., chemotherapy drugs can reach the brain.

When treating a subject using alternating electric fields, higher amplitudes are strongly associated with higher efficacy of treatment. However, as the amplitude of the alternating electric field increases, and/or as the frequency of the alternating electric field decreases (e.g., to the vicinity of 100 kHz), some subjects experience an electrosensation effect. This electrosensation could be, for example, a vibratory sensation, paresthesia, and/or a twitching or contraction sensation of muscle fibers, or a flicker of light in the eyes (phosphene). Electrosensation may discourage some subjects from continuing their treatment using alternating electric fields. Furthermore, electrosensation can limit the amplitude of the alternating electric fields that can comfortably be applied to the given subject, which in turn can limit the efficacy of the treatment.

SUMMARY OF THE INVENTION

One aspect of the invention is directed to a first method of imposing alternating electric fields in a target region of a subject's body. The first method comprises (a) imposing a first alternating electric field with a first orientation in the target region during a first interval of time. The first alternating electric field has an amplitude that increases during a plurality of first subsections of the first interval of time and either remains constant or decreases during a plurality of second subsections of the first interval of time. Each of the plurality of second subsections of the first interval of time is at least 10 ms long and comes immediately after a respective one of the first subsections of the first interval of time. The first alternating electric field has an amplitude that remains constant during a third subsection of the first interval of time. And the third subsection of the first interval of time comes after a final one of the first subsections of the first interval of time.

In some instances of the first method, the first alternating electric field has an amplitude that remains constant during each of the plurality of second subsections of the first interval of time. In some instances of the first method, the first alternating electric field has an amplitude that decreases during each of the plurality of second subsections of the first interval of time. In some instances of the first method, when the first interval of time begins, the first alternating electric field has an initial amplitude that is between 20% and 80% of the amplitude that remains constant during the third subsection of the first interval of time.

Some instances of the first method further comprise (b) imposing a second alternating electric field with a second orientation in the target region during a second interval of time. The second alternating electric field has an amplitude that increases during a plurality of first subsections of the second interval of time and either remains constant or decreases during a plurality of second subsections of the second interval of time. The second orientation and the first orientation are different. Each of the plurality of second subsections of the second interval of time is at least 10 ms long and comes immediately after a respective one of the first subsections of the second interval of time. The second alternating electric field has an amplitude that remains constant during a third subsection of the second interval of time. And the third subsection of the second interval of time comes after a final one of the first subsections of the second interval of time. These instances also comprise repeating steps (a) and (b) in an alternating sequence at least 1000 times.

Optionally, in instances of the first method described in the previous paragraph, the first alternating electric field is not imposed in the target region during an interval of time that comes immediately after the first interval of time, and the second alternating electric field is not imposed in the target region during an interval of time that comes immediately after the second interval of time.

Optionally, in instances of the first method described in the previous paragraph, the first alternating electric field has an amplitude that decreases during a fourth subsection of the first interval of time, wherein the fourth subsection of the first interval of time comes after the third subsection of the first interval of time; and the second alternating electric field has an amplitude that decreases during a fourth subsection of the second interval of time, wherein the fourth subsection of the second interval of time comes after the third subsection of the second interval of time.

Some instances of the first method further comprise (b) imposing a second alternating electric field with a second orientation in the target region during a second interval of time. The second alternating electric field has an amplitude that increases during a plurality of first subsections of the second interval of time and either remains constant or decreases during a plurality of second subsections of the second interval of time. The second orientation and the first orientation are different. Each of the plurality of second subsections of the second interval of time is at least 10 ms long and comes immediately after a respective one of the first subsections of the second interval of time. The second alternating electric field has an amplitude that remains constant during a third subsection of the second interval of time. And the third subsection of the second interval of time comes after a final one of the first subsections of the second interval of time. These instances also comprise repeating steps (a) and (b) in an alternating sequence at least 1000 times. In these instances, when the first interval of time begins, the first alternating electric field has an initial amplitude that is between 20% and 80% of the amplitude that remains constant during the third subsection of the first interval of time. And when the second interval of time begins, the second alternating electric field has an initial amplitude that is between 20% and 80% of the amplitude that remains constant during the third subsection of the second interval of time.

Another aspect of the invention is directed to a first apparatus for applying electrical signals to first, second, third, and fourth sets of at least one electrode element. The first apparatus comprises an AC signal generator and a controller. The AC signal generator has a first output, a second output, and at least one control input. And the controller is configured to apply a sequence of control signals to the at least one control input of the AC signal generator. The sequence of control signals commands the AC signal generator to (a) apply a first AC output signal to the first output during a first interval of time, wherein the first AC output signal has an amplitude that increases during a plurality of first subsections of the first interval of time and either remains constant or decreases during a plurality of second subsections of the first interval of time, wherein each of the plurality of second subsections of the first interval of time is at least 10 ms long and comes immediately after a respective one of the first subsections of the first interval of time, wherein the first AC output signal has an amplitude that remains constant during a third subsection of the first interval of time, and wherein the third subsection of the first interval of time comes after a final one of the first subsections of the first interval of time.

In some embodiments of the first apparatus, the first AC output signal has an amplitude that remains constant during each of the plurality of second subsections of the first interval of time. In some embodiments of the first apparatus, the first AC output signal has an amplitude that decreases during each of the plurality of second subsections of the first interval of time. In some embodiments of the first apparatus, when the first interval of time begins, the first AC output signal has an initial amplitude that is between 20% and 80% of the amplitude that remains constant during the third subsection of the first interval of time.

In some embodiments of the first apparatus, the sequence of control signals commands the AC signal generator to (b) apply a second AC output signal to the second output during a second interval of time, wherein the second AC output signal has an amplitude that increases during a plurality of first subsections of the second interval of time and either remains constant or decreases during a plurality of second subsections of the second interval of time, wherein each of the plurality of second subsections of the second interval of time is at least 10 ms long and comes immediately after a respective one of the first subsections of the second interval of time, wherein the second AC output signal has an amplitude that remains constant during a third subsection of the second interval of time, and wherein the third subsection of the second interval of time comes after a final one of the first subsections of the second interval of time; and (c) repeat (a) and (b) in an alternating sequence at least 1000 times.

Optionally, in the embodiments of the first apparatus described in the previous paragraph, the first AC output signal is not applied to the first output during an interval of time that comes immediately after the first interval of time, and the second AC output signal is not applied to the second output during an interval of time that comes immediately after the second interval of time.

Optionally, in the embodiments of the first apparatus described in the previous paragraph, the first AC output signal has an amplitude that decreases during a fourth subsection of the first interval of time, wherein the fourth subsection of the first interval of time comes after the third subsection of the first interval of time; and the second AC output signal has an amplitude that decreases during a fourth subsection of the second interval of time, wherein the fourth subsection of the second interval of time comes after the third subsection of the second interval of time.

In some embodiments of the first apparatus, the sequence of control signals commands the AC signal generator to (b) apply a second AC output signal to the second output during a second interval of time, wherein the second AC output signal has an amplitude that increases during a plurality of first subsections of the second interval of time and either remains constant or decreases during a plurality of second subsections of the second interval of time, wherein each of the plurality of second subsections of the second interval of time is at least 10 ms long and comes immediately after a respective one of the first subsections of the second interval of time, wherein the second AC output signal has an amplitude that remains constant during a third subsection of the second interval of time, and wherein the third subsection of the second interval of time comes after a final one of the first subsections of the second interval of time; and (c) repeat (a) and (b) in an alternating sequence at least 1000 times. In these embodiments, when the first interval of time begins, the first AC output signal has an initial amplitude that is between 20% and 80% of the amplitude that remains constant during the third subsection of the first interval of time. And when the second interval of time begins, the second AC output signal has an initial amplitude that is between 20% and 80% of the amplitude that remains constant during the third subsection of the second interval of time.

Another aspect of the invention is directed to a second method of imposing alternating electric fields in a target region of a subject's body. The second method comprises (a) imposing a first alternating electric field with a first orientation in the target region during a first interval of time. The first alternating electric field has an amplitude that increases at a first rate during a first subsection of the first interval of time and increases at a second rate that is slower than the first rate during a second subsection of the first interval of time. The second subsection of the first interval of time comes immediately after the first subsection of the first interval of time. The first alternating electric field has an amplitude that remains constant during a third subsection of the first interval of time. And the third subsection of the first interval of time comes after the second subsection of the first interval of time.

In some instances of the second method, the amplitude of the first alternating electric field increases linearly during the first subsection of the first interval of time, and the amplitude of the first alternating electric field increases linearly during the second subsection of the first interval of time. In some instances of the second method, a first derivative of the amplitude of the first alternating electric field decreases continuously during the second subsection of the first interval of time.

Some instances of the second method further comprise (b) imposing a second alternating electric field with a second orientation in the target region during a second interval of time. The second orientation and the first orientation are different. The second alternating electric field has an amplitude that increases at a third rate during a first subsection of the second interval of time and increases at a fourth rate that is slower than the third rate during a second subsection of the second interval of time. The second subsections of the second interval of time comes immediately after the first subsection of the second interval of time. The second alternating electric field has an amplitude that remains constant during a third subsection of the second interval of time. And the third subsection of the second interval of time comes after the second subsection of the second interval of time. In these instances, steps (a) and (b) are repeated in an alternating sequence at least 1000 times.

Optionally, in the instances of the second method described in the previous paragraph, the first alternating electric field is not imposed in the target region during an interval of time that comes immediately after the first interval of time, and the second alternating electric field is not imposed in the target region during an interval of time that comes immediately after the second interval of time.

Optionally, in the instances of the second method described in the previous paragraph, the first alternating electric field has an amplitude that decreases during a fourth subsection of the first interval of time, wherein the fourth subsection of the first interval of time comes after the third subsection of the first interval of time; and the second alternating electric field has an amplitude that decreases during a fourth subsection of the second interval of time, wherein the fourth subsection of the second interval of time comes after the third subsection of the second interval of time.

Another aspect of the invention is directed to a second apparatus for applying electrical signals to first, second, third, and fourth sets of at least one electrode element. The second apparatus comprises an AC signal generator and a controller. The AC signal generator has a first output, a second output, and at least one control input. The controller is configured to apply a sequence of control signals to the at least one control input of the AC signal generator, and the sequence of control signals commands the AC signal generator to (a) apply a first AC output signal to the first output during a first interval of time. The first AC output signal has an amplitude that increases at a first rate during a first subsection of the first interval of time and increases at a second rate that is slower than the first rate during a second subsection of the first interval of time. The second subsection of the first interval of time comes immediately after the first subsection of the first interval of time. The first AC output signal has an amplitude that remains constant during a third subsection of the first interval of time, and the third subsection of the first interval of time comes after the second subsection of the first interval of time.

In some embodiments of the second apparatus, the amplitude of the first AC output signal increases linearly during the first subsection of the first interval of time, and the amplitude of the first AC output signal increases linearly during the second subsection of the first interval of time. In some embodiments of the second apparatus, a first derivative of the amplitude of the first AC output signal decreases continuously during the second subsection of the first interval of time.

In some embodiments of the second apparatus, the sequence of control signals commands the AC signal generator to (b) apply a second AC output signal to the second output during a second interval of time. The second AC output signal has an amplitude that increases at a third rate during a first subsection of the second interval of time and increases at a fourth rate that is slower than the third rate during a second subsection of the second interval of time. The second subsection of the second interval of time comes immediately after the first subsection of the second interval of time. The second AC output signal has an amplitude that remains constant during a third subsection of the second interval of time. And the third subsection of the second interval of time comes after the second subsection of the second interval of time. (a) and (b) are repeated in an alternating sequence at least 1000 times.

Optionally, in the embodiments of the second apparatus described in the previous paragraph, the first AC output signal is not applied to the first output during an interval of time that comes immediately after the first interval of time, and the second AC output signal is not applied to the second output during an interval of time that comes immediately after the second interval of time.

Optionally, in the embodiments of the second apparatus described in the previous paragraph, the first AC output signal has an amplitude that decreases during a fourth subsection of the first interval of time, wherein the fourth subsection of the first interval of time comes after the third subsection of the first interval of time; and the second AC output signal has an amplitude that decreases during a fourth subsection of the second interval of time, wherein the fourth subsection of the second interval of time comes after the third subsection of the second interval of time.

Another aspect of the invention is directed to a third method of imposing alternating electric fields in a target region of a subject's body. The third method comprises (a) imposing a first alternating electric field with a first orientation in the target region during a first interval of time, the first alternating electric field having an amplitude that increases during a plurality of first subsections of the first interval of time and either remains constant or decreases during a plurality of second subsections of the first interval of time, wherein each of the plurality of second subsections of the first interval of time comes immediately after a respective one of the first subsections of the first interval of time, wherein the first alternating electric field has an amplitude that remains constant during a third subsection of the first interval of time, wherein the third subsection of the first interval of time comes after a final one of the first subsections of the first interval of time, and wherein when the first interval of time begins, the first alternating electric field has an initial amplitude that is between 20% and 80% of the amplitude that remains constant during the third subsection of the first interval of time.

Some instances of the third method further comprise (b) imposing a second alternating electric field with a second orientation in the target region during a second interval of time, the second alternating electric field having an amplitude that increases during a plurality of first subsections of the second interval of time and either remains constant or decreases during a plurality of second subsections of the second interval of time, wherein each of the plurality of second subsections of the second interval of time comes immediately after a respective one of the first subsections of the second interval of time, wherein the second alternating electric field has an amplitude that remains constant during a third subsection of the second interval of time, wherein the third subsection of the second interval of time comes after a final one of the first subsections of the second interval of time, and wherein when the second interval of time begins, the second alternating electric field has an initial amplitude that is between 20% and 80% of the amplitude that remains constant during the third subsection of the second interval of time. These instances of the third method also further comprise repeating steps (a) and (b) in an alternating sequence at least 1000 times. In these instances of the third method, the second orientation and the first orientation are different.

BRIEF DESCRIPTION OF THE DRAWINGS

Various embodiments are described in detail below with reference to the accompanying drawings, wherein like reference numerals represent like elements.

DESCRIPTION OF THE PREFERRED EMBODIMENTS

Figure 1:
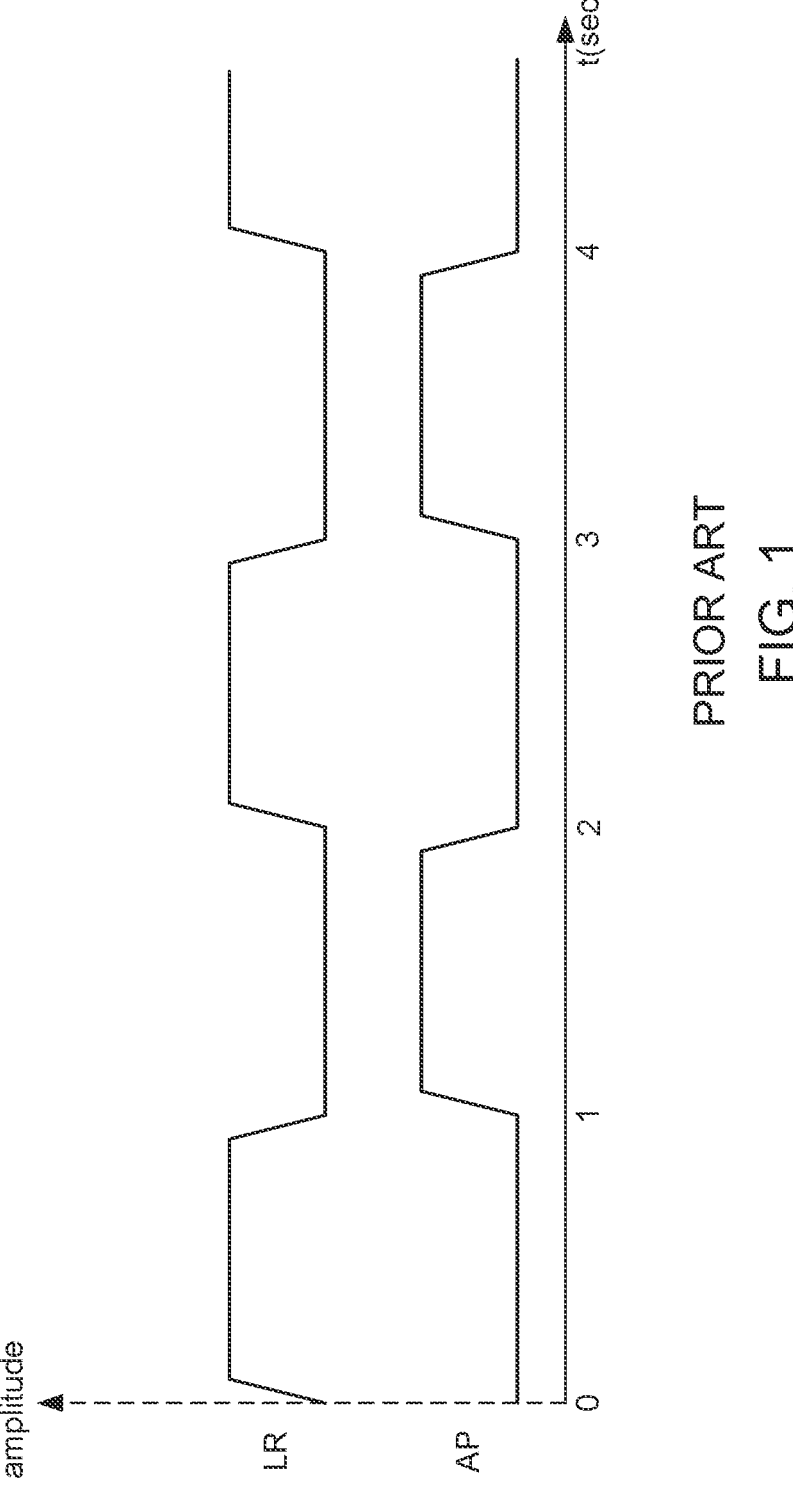
FIG. 1 depicts the AC output amplitudes in two channels of the prior art Optune® system

FIG. 1 depicts the AC output amplitudes of the L/R channel and the A/P channel in the prior art Optune® system. Notably, when the signal to either the A/P or L/R transducer arrays is turned on during any given one-second interval, the amplitude of the AC voltage does not jump immediately to its peak value. Instead, the amplitude of the AC voltage ramps up from zero to its peak over the course of a 50 ms window. Similarly, when the signal is turned off during any given one-second interval, the amplitude of the AC voltage ramps down from its peak to zero over the course of a 50 ms window.

The inventors have determined that electrosensation is not a problem during steady-state application of an AC voltage to a given pair of transducer arrays, or when the AC voltage turns off/ramps down. Instead, electrosensation appears to only be a problem when the AC voltage turns on/ramps up (which occurs when the system is first turned on and each time the electric field switches direction). The electrosensation is believed to originate from interactions between the alternating electric fields and nerve cells or fibers (i.e., neurons or axons) that are positioned near or adjacent to the transducer arrays.

The inventors have also determined that electrosensation can be ameliorated by changing the way the trajectory of how the AC voltage increases from zero to its peak when the AC voltage is first applied to any given pair of transducer arrays, and also when the alternating electric field switches direction.

Figure 2:
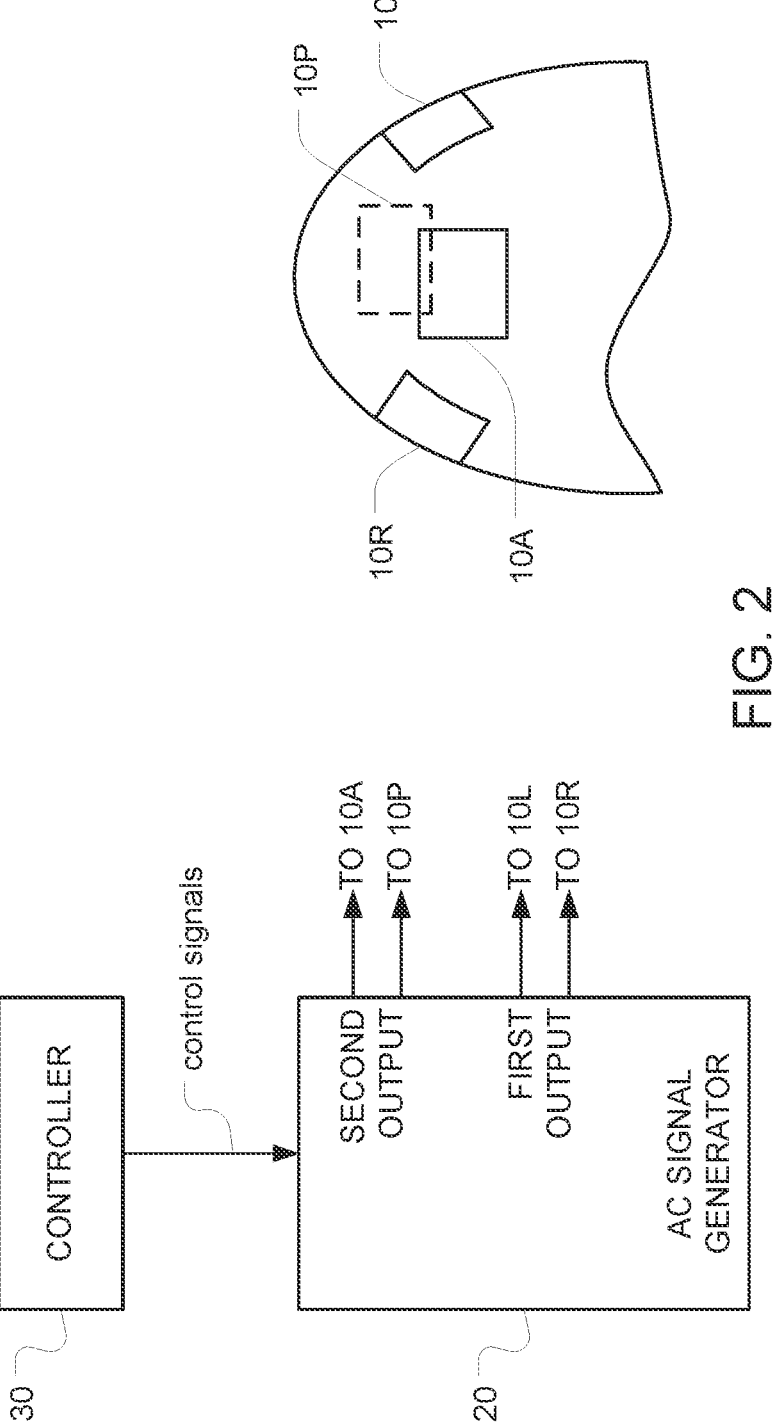
FIG. 2 is a block diagram of a system for driving a set of transducer arrays with AC voltage signals in which the amplitude trajectory of the AC outputs can be controlled.

FIG. 2 is a block diagram of a system for driving a set of transducer arrays with AC voltage signals in which the trajectory of how the AC voltage increases from zero to its peak can be controlled. The system includes an AC signal generator 20 that is designed to generate first and second AC outputs at a frequency between 50 kHz and 10 MHz (e.g., 50 kHz-1 MHz, 50-500 kHz, 75-300 kHz, or 150-250 kHz). When the system is used to apply TTFields to a person's body (as shown in FIG. 2), the first AC output is applied across a first pair of transducer arrays 10L and 10R that are positioned to the left and right of the tumor; and the second AC output is applied across a second pair of transducer arrays 10A and 10P that are positioned anterior and posterior to the tumor.

When the AC signal generator 20 applies a voltage between transducer arrays 10L, 10R, an alternating electric field is induced through the target region with field lines that run generally from left to right. And when the AC signal generator 20 applies a voltage between transducer arrays 10A, 10P, an alternating electric field is induced through the target region with field lines that run generally from front to back. The frequency of the alternating electric field will match the frequency of the AC signal generator 20. The electrode elements in the transducer arrays 10 can be capacitively-coupled electrode elements (i.e., electrode elements that include a thin dielectric layer that contacts the subject's body) or conductive electrode elements (i.e., electrode elements that include a conductive surface that contacts the subject's body).

In some embodiments, the voltage generated by the AC signal generator 20 is sufficient to induce an electric field of at least 1 V/cm in at least a portion of the cells. In some embodiments, the voltage generated by the AC signal generator 20 is sufficient to induce an electric field of 1-10 V/cm in at least a portion of the cells.

As in the prior art Optune® system, (a) the first AC output is applied to the L/R transducer arrays for 1 second; (b) the second AC output is applied to the A/P transducer arrays for 1 second; and the two-step sequence (a) and (b) is repeated for the duration of the treatment. But the trajectory of how the AC voltage increases from zero to its peak in the FIG. 2 embodiment differs from the ramp-up trajectory used in Optune® in a manner that helps ameliorate the electrosensation that is experienced by the subject.

The AC signal generator 20 is configured to generate first and second AC outputs with amplitudes that depend on a state of at least one control input. A controller 30 rapidly sends sequential control signals (e.g., at a rate of 1 control signal per ms) to the at least one control input to generate the amplitude trajectories described herein. Note that although FIG. 2 depicts the controller 30 and the AC signal generator 20 as two distinct blocks, those two blocks may be integrated into a single hardware device.

The details of the construction of the controller 30 and the nature of the control signals will depend on the design of the AC signal generator 20. In one example, the design of the AC signal generator 20 is similar to the AC signal generator described in U.S. Pat. No. 9,910,453, which is incorporated herein by reference in its entirety. This particular AC signal generator has two output channels (i.e., a first channel for L/R and a second channel for A/P). The instantaneous AC output voltage on either channel depends on the instantaneous output voltage of a DC-DC converter, and the output voltage of that DC-DC converter is controlled by writing control words to a digital-to-analog converter (DAC), e.g., at a rate of 1 control signal per ms.

This AC signal generator can therefore be used to increase the AC output voltage at any desired rate and with any trajectory by sequentially sending appropriate control words to the DAC.

Figure 3:
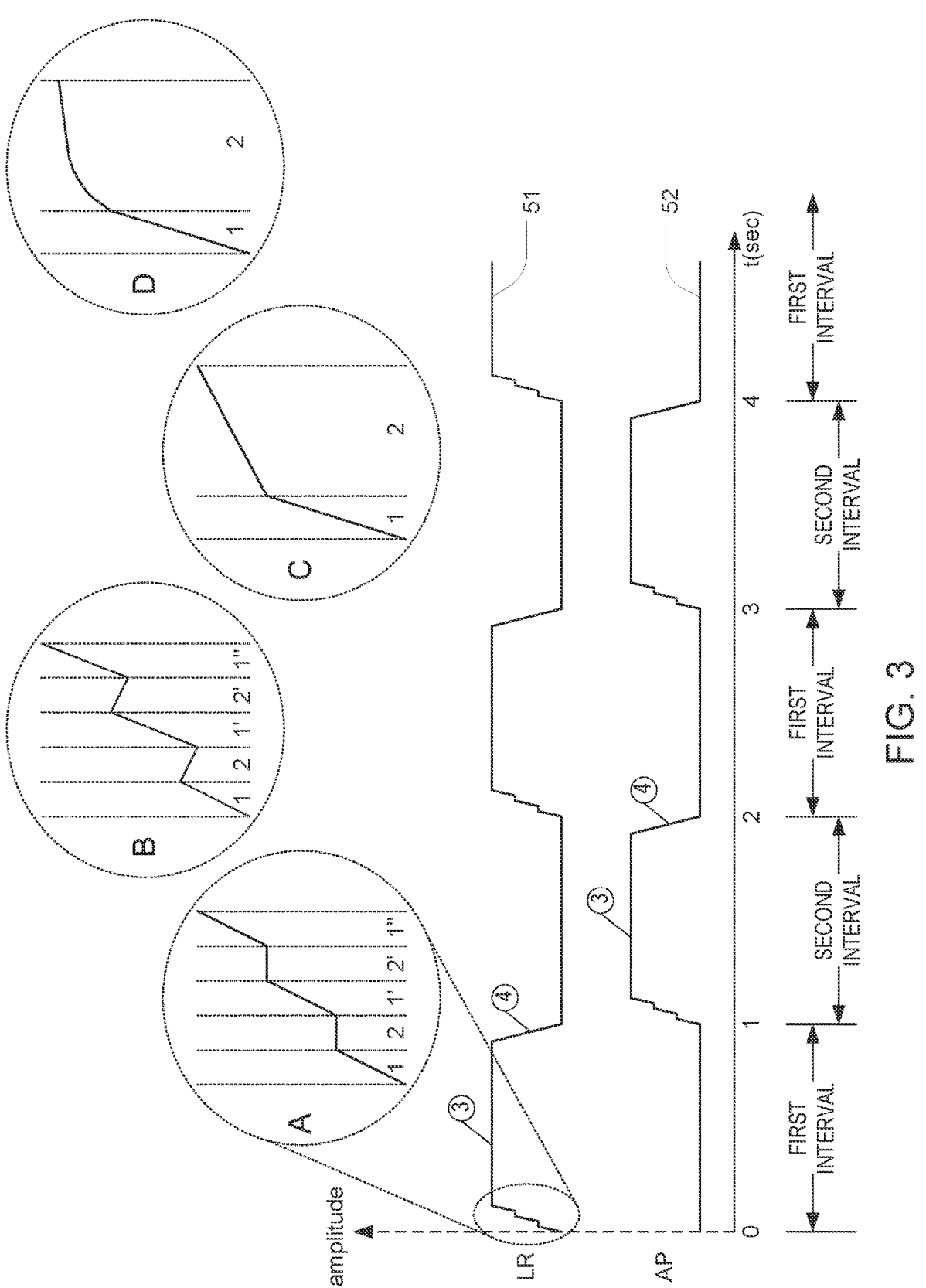
FIG. 3 depicts examples of amplitude trajectories that can be imparted on the outputs of the AC signal generator to ameliorate electrosensation.

FIG. 3 depicts one example of an amplitude trajectory that may be imparted on the L/R and A/P output channels of the AC signal generator 20 (shown in FIG. 2) to ameliorate electrosensation. More specifically, trace 51 depicts how the amplitude of the AC voltage of the L/R channel varies over time, and trace 52 depicts how the amplitude of the AC voltage of the A/P channel varies over time. Panel A is a magnified version of the ramp-up section of trace 51 for the L/R channel. In this example, the amplitude increases during interval 1, then remains constant during interval 2 for at least 10 ms, then increases further during interval 1', then remains constant during interval 2' for at least 10 ms, then increases further during interval 1". To generate this amplitude trajectory, the controller 30 sequentially sends control words (e.g., once per ms) to the AC signal generator 20. When the AC signal generator 20 receives these control words, it will generate an output with an amplitude that resembles the waveform depicted in panel A of FIG. 3. A similar sequence of control words is used to control the A/P channel. Note that if the controller 30 sends control words to the AC signal generator at a rate of one control word per ms, the intervals 1, 1', 1" will not be true ramps (as depicted in FIG. 3). Instead, those intervals will be staircases with very small stair heights which, in a zoomed-out view, will resemble the ramps depicted in FIG. 3.

When the output of the AC signal generator 20 is applied to the transducer arrays 10L, 10R, a first alternating electric field with a first orientation is imposed in the target region during a first interval of time. The first alternating electric field has an amplitude that increases during a plurality of first subsections 1, 1', 1" of the first interval of time and remains constant for at least 10 ms during a plurality of second subsections 2, 2' of the first interval of time. Each of the plurality of second subsections 2, 2' of the first interval of time comes immediately after a respective one of the first subsections 1, 1' of the first interval of time. The rationale for including the second subsections 2, 2' of the first interval of time (each of which is at least 10 ms long) in the trajectory is to allow the subject to get used to a given voltage setting before the voltage is increased further. In some embodiments, each of these intervals is at least 20 ms or at least 40 ms long.

Note that while the first subsections 1, 1', 1" of the first interval of time in the example depicted in panel A collectively occupy more than half of the first interval of time, the first subsections 1, 1', 1" (during which the amplitude rises) can be significantly shorter. For example, in some embodiments these subsections can be as short as 1 ms, as short as 1 μs, or even shorter than 1 μs. And because each of the second subsections 2, 2' is much longer (i.e., at least 10 ms long) in these embodiments, the resulting waveform during the first interval of time will resemble a staircase with vertical edges. In these embodiments, the transition from one amplitude to the next can be accomplished by writing a single control word to the AC signal generator 20. When the AC signal generator 20 receives the single control word, its output will jump as fast as it can to the next step of the staircase, limited only by the response time of the AC signal generator 20, which can be as short as 1 μs, or even shorter than 1 μs. In these embodiments, the duration of each first subsection 1, 1', 1" will be correspondingly short.

After the ramp-up period (which includes subsections 1, 2, 1', 2', and 1" of the first interval of time), the output of the AC signal generator 20 remains constant during interval 3. Interval 3 comes after the final one of the first subsections 1". After interval 3, the output of the AC signal generator 20 ramps down during interval 4. When the output of the AC signal generator 20 is applied to the transducer arrays 10L, 10R, the first alternating electric field will have an amplitude that remains constant during a third subsection 3 of the first interval of time. The third subsection 3 of the first interval of time comes after (although not *immediately* after in this example) a final one of the first subsections 1" of the first interval of time.

Operation of the anterior/posterior channel (and the second alternating electric field) is similar to the operation for the left/right channel (and the first alternating electric field) described above, except that the two channels are activated in an alternating sequence (e.g., at least 1000 times) and are out of phase. When one channel is active, the other channel is off. As a result, the first alternating electric field is not imposed in the target region during an interval of time that comes immediately after the first interval of time, and the second alternating electric field is not imposed in the target region during an interval of time that comes immediately after the second interval of time.

A wide variety of alternative designs for the AC signal generator 20 and the controller 30 can be substituted for the example provided above, as long as the controller 30 has the ability to control the AC signal generator 20. For example, if the AC signal generator is designed to respond to an analog control signal, the controller 30 must generate whatever sequence of analog control signals is needed to cause the AC signal generator 20 to output the desired waveforms. In this situation, the controller 30 could be implemented using a microprocessor or microcontroller that is programmed to write appropriate control words to a digital-to-analog converter, the output of which generates the analog control signals that cause the AC signal generator 20 to generate the desired waveforms. Alternatively, the controller 30 could be implemented using an analog circuit that automatically generates the appropriate sequence of control signals (which are then applied to the control input of the AC signal generator).

The trajectory of how the AC voltage increases from zero to its peak depicted in panel A of FIG. 3 is not the only trajectory that can be used to ameliorate electrosensation. To the contrary, a variety of alternative trajectories can be used. One example of an alternative trajectory that can be used to ameliorate electrosensation is depicted in panel B of FIG. 3. This example is similar to the embodiment described above in connection with panel A of FIG. 3, except that instead of remaining constant for at least 10 ms during intervals 2 and 2', the amplitude of the AC signal generator 20 decreases for at least 10 ms during intervals 2 and 2'. To generate this amplitude trajectory, the controller 30 sequentially sends control words (e.g., once per millisecond) to the AC signal generator 20. When the AC signal generator 20 receives these control words, it will generate an output with an amplitude that resembles the waveform depicted in panel B of FIG. 3. A similar sequence of control words is used to control the A/P channel.

When the output of the AC signal generator 20 is applied to the transducer arrays 10L, 10R in these embodiments, a first alternating electric field with a first orientation is imposed in the target region during a first interval of time. The first alternating electric field has an amplitude that increases during a plurality of first subsections 1, 1', 1" of the first interval of time and decreases for at least 10 ms during a plurality of second subsections 2, 2' of the first interval of time. Each of the plurality of second subsections 2, 2' of the first interval of time comes immediately after a respective one of the first subsections 1, 1' of the first interval of time. A similar sequence occurs at the A/P channel. Here again, the rationale for including the second subsections 2, 2' of the first interval of time (each of which is at least 10 ms long) in the trajectory is to allow the subject to get used to a given voltage setting before the voltage is increased further. In some embodiments, each of these intervals is at least 20 ms or at least 40 ms long.

Panel C of FIG. 3 depicts another example of a trajectory of how the AC voltage increases from zero to its peak that can be used to ameliorate the electrosensation that is experienced by a subject. This example is similar to the embodiment described above in connection with panel A of FIG. 3, except that the amplitude of the AC signal generator 20 increases at a first rate during a first subsection 1 of the first interval of time and increases at a second rate that is slower than the first rate during a second subsection 2 of the first interval of time. The increase during the first subsection of the first interval of time can be a linear increase (as depicted in panel C) or a nonlinear increase. Similarly, the increase during the second subsection of the first interval of time can be a linear increase (as depicted in panel C) or a nonlinear increase (as depicted in panel D).

The second subsection of the first interval of time comes immediately after the first subsection of the first interval of time. The third and fourth subsections of the first interval of time in this embodiment are similar to the corresponding subsections of the panel A embodiment described above. To generate this amplitude trajectory, the controller 30 sequentially sends control words (e.g., once per millisecond) to the AC signal generator 20. When the AC signal generator 20 receives these control words, it will generate an output with an amplitude that resembles the waveform depicted in panels C or D of FIG. 3. A similar sequence of control words is used to control the A/P channel.

When the output of the AC signal generator 20 is applied to the transducer arrays 10L, 10R in these embodiments, a first alternating electric field with a first orientation is imposed in the target region during a first interval of time. The first alternating electric field has an amplitude that increases at a first rate during a first subsection 1 of the first interval of time and increases at a second rate that is slower than the first rate during a second subsection 2 of the first interval of time. A similar sequence occurs at the A/P channel.

In the examples described above, the AC voltage generator 20 is configured to increase its output voltage using the same trajectory every time (e.g., either (a) always using the trajectory described above in connection with panel A in FIG. 3; (b) always using the trajectory described above in connection with panel B; (c) always using the trajectory described above in connection with panel C; or (d) always using the trajectory described above in connection with panel D). But in alternative embodiments, the AC voltage generator 20 can be configured to control the trajectory of how the AC voltage increases from zero to its peak in different ways at different times. For example, by using the panel A and panel B trajectories at different times; by using the panel A and panel C trajectories at different times; by using the panel A, panel B, and panel C trajectories at different times; or by using the panel A, panel B, panel C, and panel D trajectories at different times; etc.

In all the examples depicted in FIG. 3, the amplitude of the AC signal generator's first and second outputs are both very small (e.g., less than 1% of the constant level that is applied during the third subsection of the respective interval of time) when the first and second intervals of time begin. Similarly, the first and second alternating electric fields are both very small (e.g., less than 1% of the level that is applied during the third subsection of the respective interval of time) when the first and second intervals of time begin.

Figure 4:
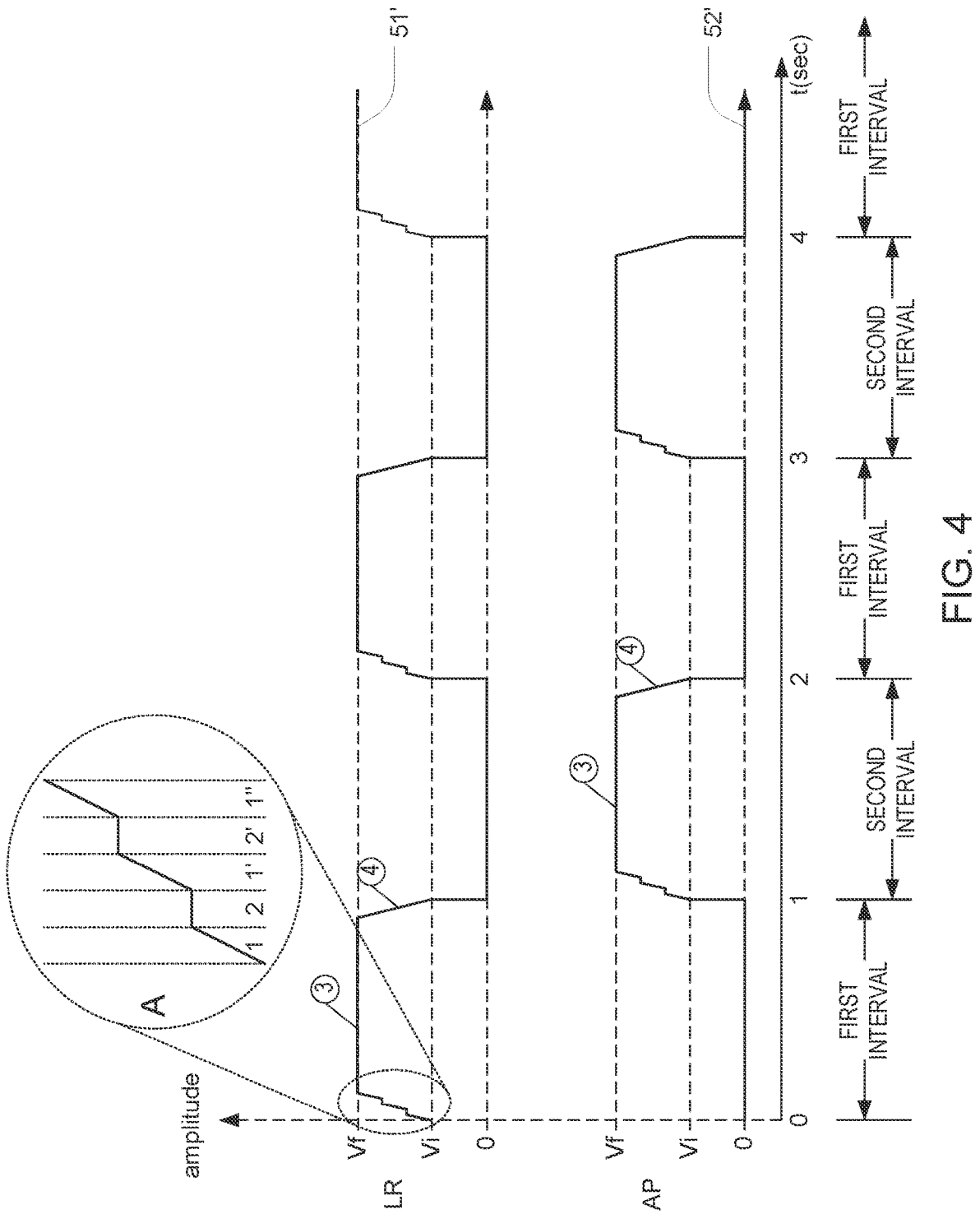
FIG. 4 depicts additional examples of amplitude trajectories that can be imparted on the outputs of the AC signal generator to ameliorate electrosensation.

But in alternative embodiments (e.g., as depicted in FIG. 4), the amplitude of the AC signal generator's first and second outputs can jump immediately to an initial level Vi that is 20-80% of the constant level Vf that is applied during the third subsection of the respective interval of time. Similarly, the amplitude of the first and second alternating electric fields can jump immediately to an initial level Vi that is 20-80% of the constant level Vf that is applied during the third subsection of the respective interval of time. After the initial jump to the initial level Vi, the amplitude increases from Vi to Vf using, for example, the trajectory depicted in panel A of FIG. 4 (which is similar to the trajectory in panel A of FIG. 3, but offset by Vi). Moreover, these embodiments are not limited to the single amplitude trajectory depicted in panel A. To the contrary, a variety of other trajectories for changing the amplitude after making an initial jump to Vi may be used in place of the trajectory depicted in panel A, including but not limited to the amplitude trajectories depicted in panels B, C, and D of FIG. 3 (but with an added offset of Vi).

These embodiments are advantageous because electrosensation is relatively rare when the voltage is below a threshold level (e.g., 40 V). Accordingly, jumping immediately (e.g., in less than 200 μs) from 0 V to an initial voltage Vi (e.g., 40 V) when the first and second intervals of time begin (as depicted in FIG. 4) will not cause electrosensation in the vast majority of patients. And because time is not wasted ramping up from 0 V to Vi, more time will be available to ramp up from Vi to the final voltage Vf (which can be e.g., over 100 V). This will advantageously (a) increase the average field strength that is applied to the subject and (b) provide the subject with more time to get used to each new voltage level before the voltage increases to the next level, thereby further ameliorating electrosensation.

In some embodiments, the value of the initial level Vi will be the same for all patients (e.g., 40 V). In other embodiments, the value of the initial level Vi can be patient-specific, and can be set via a suitable user interface that communicates with the controller 30. In the latter embodiments, the controller 30 can be programmed to apply different voltage levels to the subject in order to determine the threshold voltage Vth where electrosensation begins for the particular subject that will be treated. The initial level Vi is then set below that threshold Vth during the course of treatment for that particular subject.

These embodiments, in which the amplitude jumps to an initial level of Vi are similar to the embodiments described above in connection with FIGS. 2-3 with two exceptions. First, at the beginning of each first interval and each second interval, the amplitude jumps immediately to an initial level Vi, and then follows a subsequent trajectory until it reaches the final level Vf. And second, the durations of (a) each of the plurality of second subsections of the first interval of time and (b) each of the plurality of second subsections of the second interval of time can be either (i) at least 10 ms (as described above in connection with FIG. 2-3) or less than 10 ms (e.g., 5-10 ms, or even less than 5 ms).

In the examples described above, the direction of the alternating electric fields was switched every one second between the L/R and A/P channels, which means that each interval of time is 1 second long. But in alternative embodiments, the direction of the alternating electric fields can be switched at a faster rate (e.g., every 1-1000 ms) or at a slower rate (e.g., every 1-360 seconds), in which case the duration of each interval would be shorter or longer than 1 second. Optionally, the overall duration of treatment may be interrupted by breaks.

In the examples described above, the direction of the alternating electric fields was switched between two directions. But in alternative embodiments the direction of the alternating electric fields may be switched between three or more directions (assuming that additional pairs of transducer arrays are provided). For example, the direction of the alternating electric fields may be switched between three directions, each of which is determined by the placement of its own pair of transducer arrays. In other alternative embodiments, the transducer arrays need not be arranged in pairs. See, for example, the transducer array positioning described in U.S. Pat. No. 7,565,205, which is incorporated herein by reference. But regardless of the arrangement of the transducer arrays, one of the modified trajectories described herein is used every time a given transducer array is activated.

In some anatomic locations, the transducer arrays are not positioned on the subject's skin. Instead, the transducer arrays are implanted into the subject's body (e.g., just beneath the subject's skin) so that application of an AC voltage between the transducer arrays will impose the alternating electric fields in a target region of the subject's body.

Finally, in some anatomic locations, instead of switching the orientation of the alternating electric field back and forth between two or more different directions, an electric field with a constant orientation may be used. Embodiments for use with these locations are similar to the FIG. 2 embodiment, except that the AC signal generator 20 has only a single output (e.g., only the L/R output). In these embodiments, the AC voltage generator is configured to, when initially switched on, increase its output voltage using any of the trajectories described above (e.g., in connection with panels A, B, C, or D in FIG. 3), and then either leave its output voltage at a fixed level for the duration of the treatment, or switch the single output on and off repeatedly (e.g., on for 1-10 s and off for 0.1-10 s). In the latter situation, each time the AC voltage generator switches back on, it increases its output voltage using any of the trajectories described above (e.g., in connection with panels A, B, C, or D in FIG. 3).

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A method of imposing alternating electric fields in a target region of a subject's body, the method comprising:

(a) imposing a first alternating electric field with a first orientation in the target region during a first interval of time, the first alternating electric field having an amplitude that increases during a plurality of first subsections of the first interval of time and either remains constant or decreases during a plurality of second subsections of the first interval of time, wherein each of the plurality of second subsections of the first interval of time is at least 10 ms long and comes immediately after a respective one of the first subsections of the first interval of time, wherein the first alternating electric field has an amplitude that remains constant during a third subsection of the first interval of time, and wherein the third subsection of the first interval of time comes after a final one of the first subsections of the first interval of time.

2. The method of claim 1, wherein when the first interval of time begins, the first alternating electric field has an initial amplitude that is between 20% and 80% of the amplitude that remains constant during the third subsection of the first interval of time.

3. The method of claim 1, further comprising:

(b) imposing a second alternating electric field with a second orientation in the target region during a second interval of time, the second alternating electric field having an amplitude that increases during a plurality of first subsections of the second interval of time and either remains constant or decreases during a plurality of second subsections of the second interval of time, wherein each of the plurality of second subsections of the second interval of time is at least 10 ms long and comes immediately after a respective one of the first subsections of the second interval of time, wherein the second alternating electric field has an amplitude that remains constant during a third subsection of the second interval of time, and wherein the third subsection of the second interval of time comes after a final one of the first subsections of the second interval of time; and repeating steps (a) and (b) in an alternating sequence at least 1000 times, wherein the second orientation and the first orientation are different.

4. The method of claim 3, wherein the first alternating electric field is not imposed in the target region during an interval of time that comes immediately after the first interval of time, and wherein the second alternating electric field is not imposed in the target region during an interval of time that comes immediately after the second interval of time.

5. The method of claim 3, wherein the first alternating electric field has an amplitude that decreases during a fourth subsection of the first interval of time, wherein the fourth subsection of the first interval of time comes after the third subsection of the first interval of time, wherein the first alternating electric field is not imposed in the target region during an interval of time that comes immediately after the first interval of time, wherein the second alternating electric field has an amplitude that decreases during a fourth subsection of the second interval of time, wherein the fourth subsection of the second interval of time comes after the third subsection of the second interval of time, and wherein the second alternating electric field is not imposed in the target region during an interval of time that comes immediately after the second interval of time.

6. The method of claim 3, wherein when the first interval of time begins, the first alternating electric field has an initial amplitude that is between 20% and 80% of the amplitude that remains constant during the third subsection of the first interval of time, and wherein when the second interval of time begins, the second alternating electric field has an initial amplitude that is between 20% and 80% of the amplitude that remains constant during the third subsection of the second interval of time.

7. An apparatus for applying electrical signals to first, second, third, and fourth sets of at least one electrode element, the apparatus comprising:

an AC signal generator having a first output, a second output, and at least one control input; and a controller configured to apply a sequence of control signals to the at least one control input of the AC signal generator, wherein the sequence of control signals commands the AC signal generator to (a) apply a first AC output signal to the first output during a first interval of time, wherein the first AC output signal has an amplitude that increases during a plurality of first subsections of the first interval of time and either remains constant or decreases during a plurality of second subsections of the first interval of time, wherein each of the plurality of second subsections of the first interval of time is at least 10 ms long and comes immediately after a respective one of the first subsections of the first interval of time, wherein the first AC output signal has an amplitude that remains constant during a third subsection of the first interval of time, and wherein the third subsection of the first interval of time comes after a final one of the first subsections of the first interval of time.

8. The apparatus of claim 7, wherein the first AC output signal has an amplitude that remains constant during each of the plurality of second subsections of the first interval of time.

9. The apparatus of claim 7, wherein the first AC output signal has an amplitude that decreases during each of the plurality of second subsections of the first interval of time.

10. The apparatus of claim 7, wherein when the first interval of time begins, the first AC output signal has an initial amplitude that is between 20% and 80% of the amplitude that remains constant during the third subsection of the first interval of time.

11. The apparatus of claim 7, wherein the sequence of control signals commands the AC signal generator to:

(b) apply a second AC output signal to the second output during a second interval of time, wherein the second AC output signal has an amplitude that increases during a plurality of first subsections of the second interval of time and either remains constant or decreases during a plurality of second subsections of the second interval of time, wherein each of the plurality of second subsections of the second interval of time is at least 10 ms long and comes immediately after a respective one of the first subsections of the second interval of time, wherein the second AC output signal has an amplitude that remains constant during a third subsection of the second interval of time, and wherein the third subsection of the second interval of time comes after a final one of the first subsections of the second interval of time, and repeat (a) and (b) in an alternating sequence at least 1000 times.

12. The apparatus of claim 11, wherein the first AC output signal is not applied to the first output during an interval of time that comes immediately after the first interval of time, and wherein the second AC output signal is not applied to the second output during an interval of time that comes immediately after the second interval of time.

13. The apparatus of claim 11, wherein the first AC output signal has an amplitude that decreases during a fourth subsection of the first interval of time, wherein the fourth subsection of the first interval of time comes after the third subsection of the first interval of time, wherein the first AC output signal is not applied to the first output during an interval of time that comes immediately after the first interval of time, wherein the second AC output signal has an amplitude that decreases during a fourth subsection of the second interval of time, wherein the fourth subsection of the second interval of time comes after the third subsection of the second interval of time, and wherein the second AC output signal is not applied to the second output during an interval of time that comes immediately after the second interval of time.

14. The apparatus of claim 11, wherein when the first interval of time begins, the first AC output signal has an initial amplitude that is between 20% and 80% of the amplitude that remains constant during the third subsection of the first interval of time, and wherein when the second interval of time begins, the second AC output signal has an initial amplitude that is between 20% and 80% of the amplitude that remains constant during the third subsection of the second interval of time.

\* \* \* \* \*